United States Patent
Gower et al.

(10) Patent No.: US 7,455,854 B2
(45) Date of Patent: Nov. 25, 2008

(54) METHOD FOR PRODUCING A MINERAL FIBER

(75) Inventors: Laurie B. Gower, Gainesville, FL (US); Matthew J. Olszta, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 389 days.

(21) Appl. No.: 10/819,040

(22) Filed: Apr. 5, 2004

(65) Prior Publication Data

US 2005/0152990 A1 Jul. 14, 2005

Related U.S. Application Data

(63) Continuation-in-part of application No. 10/691,002, filed on Oct. 22, 2003, and a continuation-in-part of application No. 10/418,843, filed on Apr. 18, 2003.

(60) Provisional application No. 60/373,801, filed on Apr. 18, 2002.

(51) Int. Cl.
*A61F 2/00* (2006.01)
*A61F 13/00* (2006.01)
*A61K 9/00* (2006.01)
*A61K 9/70* (2006.01)
*C12N 11/00* (2006.01)
*C12N 11/14* (2006.01)

(52) U.S. Cl. ............... 424/423; 424/400; 424/443; 435/174; 435/176

(58) Field of Classification Search ............ None
See application file for complete search history.

(56) References Cited

U.S. PATENT DOCUMENTS

| | | | |
|---|---|---|---|
| 4,774,227 A | 9/1988 | Piez et al. | |
| 4,795,467 A | 1/1989 | Piez et al. | |
| 4,865,602 A | 9/1989 | Smestad et al. | |
| 4,880,610 A | 11/1989 | Constantz | |
| 5,147,507 A | 9/1992 | Gill | |
| 5,178,845 A | 1/1993 | Constantz et al. | |
| 5,273,964 A | 12/1993 | Lemons | |
| 5,418,222 A | 5/1995 | Song et al. | |
| 5,455,231 A | 10/1995 | Constantz et al. | |
| 5,532,217 A | 7/1996 | Silver et al. | |
| 5,593,488 A | 1/1997 | Wu | |
| 5,800,541 A | 9/1998 | Rhee et al. | |
| 6,071,336 A | 6/2000 | Fairchild et al. | |
| 6,190,633 B1 | 2/2001 | Takahashi et al. | |
| 6,201,039 B1 | 3/2001 | Brown et al. | |
| 6,300,315 B1 | 10/2001 | Liu | |
| 6,592,712 B2 | 7/2003 | Koukoulas et al. | |
| 6,627,170 B2 | 9/2003 | Takahashi et al. | |
| 6,995,013 B2 | 2/2006 | Connelly et al. | |
| 2003/0059362 A1 | 3/2003 | Takahashi et al. | |
| 2003/0094252 A1 | 5/2003 | Sundar et al. | |
| 2003/0232071 A1 | 12/2003 | Gower et al. | |
| 2004/0020410 A1 | 2/2004 | Gane et al. | |
| 2004/0052865 A1 | 3/2004 | Gower et al. | |
| 2004/0131562 A1 | 7/2004 | Gower et al. | |

FOREIGN PATENT DOCUMENTS

| | | |
|---|---|---|
| EP | 0 143 363 B1 | 6/1985 |
| EP | 0 233 770 B1 | 5/1990 |
| EP | 0 197 693 B1 | 10/1991 |
| EP | 0 270 254 B1 | 3/1993 |
| WO | WO 03/035127 A1 | 5/2003 |
| WO | WO 03/089022 A1 | 10/2003 |

OTHER PUBLICATIONS

Addadi, L. and S. Weiner "Control and Design Principles in Biological Mineralization" *Angew. Chem. Int. Ed. Engl.* 1992, 31:153-169.
Addadi, L. et al. "A Chemical Model for the Cooperation of Sulfates and Carboxylates in Calcite Crystal Nucleation: Relevance to Biomineralization" *PNAS USA*, May 1, 1987, 84(9):2732-2736.
Addadi, L. et al. "Growth and Dissolution of Organic Crystals with 'Tailor-Made' Inhibitors—Implications in Stereochemistry and Materials Science" *Angew. Chem. Int. Ed. Engl.*, 1985, 24:466-485.
Addadi, S. and S. Weiner "Interactions between Acidic Proteins and Crystals: Stereochemical Requirements in Biomineralization" *PNAS USA*, Jun. 15, 1985, 82(12):4110-4114.
Aizenberg, J. "Patterned crystallization of calcite in vivo and in vitro" *J. Crystal Growth*, 2000, 211:143-148.
Bianco, P. "Structure and Mineralization of Bone" in Calcification in Biological Systems, Bonnuci, E., Ed., Chapter 11, pp. 243-268, 1992, CRC Press, Inc., Boca Raton, FL.
Bradt, J-H. et al. "Biomimetic Mineralization of Collagen by Combined Fibril Assembly and Calcium Phosphate Formation" *Chem. Mater.*, 1999, 11:2694-2701.
Carlson, S.J. "Vertebrate Dental Structures" in Skeletal Biomineralization: Patterns, Processes and Evolutionary Trends Carter, J.G., Ed., Chapter 21, pp. 531-556, 1990, Van Nostrand Reinhold, New York, NY.
Deng, Y. et al. "Study on the three-dimensional proliferation of rabbit articular cartilage-derived chondrocytes on polyhydroxyalkanoate scaffolds" *Biomaterials*, 2002, 23:4049-4056.
Dickinson, R.B. et al. "Biased Cell Migration of Fibroblasts Exhibiting Contact Guidance in Oriented Collagen Gels" *Annals. Biomed. Engin.*, 1994, 22:342-356.

(Continued)

*Primary Examiner*—David M Naff
(74) *Attorney, Agent, or Firm*—Saliwanchik, Lloyd & Saliwanchik (57) ABSTRACT

The present invention pertains to mineral fibers useful as biomimetics of tissue, such as dental enamel and bone, and as filler in paper, paint, coatings, and plastic production. The present invention also concerns methods for producing mineral fibers by contacting an inorganic liquid-phase mineral precursor with a crystalline inorganic substrate under conditions permitting the inorganic liquid-phase mineral precursor to solidify and crystallize, compositions comprising mineral fibers, and methods for treating a tissue defect within a patient by applying mineral fibers to the site of the tissue defect.

33 Claims, 6 Drawing Sheets

OTHER PUBLICATIONS

Francillon-Vieillot, H. et al. "Microstructure and Mineralization of Vertebrate Skeletal Tissues" in Skeletal Biomineralization: Patterns, Processes and Evolutionary Trends Carter, J.G., Ed., Chapter 20, pp. 471-530, 1990, Van Nostrand Reinhold, New York, NY.

Gower, L. and D. Odom "Deposition of calcium carbonate films by a polymer-induced liquid-precursor (PILP) process" *J. Crystal Growth*, 2000, 210:719-734.

Gower, L. and D. Tirrell "Calcium carbonate films and helices grown in solutions of poly(aspartate)" *J. Crystal. Growth*, 1998, 191:153-160.

Gower, L. "The Influence of Polyaspartate Additive on the Growth and morphology of Calcium Carbonate Crystals" Doctoral Dissertation, 1997, University of Massachusetts at Amherst.

Greenfield, E.M. et al. "Ionotropic Nucleation of Calcium Carbonate by Molluscan Matrix" *Amer. Zool.*, 1984, 24:925-932.

Guido, S. and R. Tranquillo "A methodology for the systematic and quantitative study of cell contact guidance in oriented collagen gels" *J. Cell Sci.*, 1993, 105:317-331.

Jones, D. and U. Walter "The Silicate Garden Reaction in Microgravity: A Fluid Interfacial Instability" *J. Colloid and Interface Sci.*, 1998, 203:286-293.

Katz, E.P. et al. "The Structure of Mineralized Collagen Fibrils" *Connective Tissue Res.*, 1989, 21:149-158.

Landis, W.J. et al. "Mineral and Organic Matrix Interaction in Normally Calcifying Tendon Visualized in Three Dimensions by High-Voltage Electron Microscopic Tomography and Graphic Image Reconstruction" *J. Struct. Biol.*, 1993, 110:39-54.

Landis, W.J. et al. "Topographic Imaging of Mineral and Collagen in the Calcifying Turkey Tendon" *Connective Tissue Res.*, 1991, 25:181-196.

Mann, S. "Mineralization in Biological Systems" *Structure and Bonding*, 1983, 54:125-174.

Mann, S. "Crystallochemical Strategies in Biomineralization" in Biomineralization: Chemical and Biochemical Perspectives, Mann, S et al., Eds., Chapter 2, pp. 35-62, 1989, VCH Publishers, New York, N.Y.

Murthy, N.S. "Liquid Crystallinity in Collagen Solutions and Magnetic Orientation of Collagen Fibrils" *Biopolymers*, 1984, 23:1261-1267.

Nehrer, S. et al. "Chondrocyte-seeded collagen matrices implanted in a chondral defect in a canine model" *Biomaterials*, 1998, 19:2313-2328.

Oh, Y.R. and O.O. Park "Transient Flow Birefringence of Calf Skin Collagen Solutions" *J. Chem. Eng. Jpn.*, 1992, 25(3):243-250.

Olszta, M.J. et al. "A New Paradigm for Biomineral Formation: Mineralization via an Amorphous Liquid-Phase Precursor" *Connective Tissue Res.*, 2003, 44(Suppl. 1):326-334.

Olszta, M. "Biomimetic Mineralization of Collagen for Nanostructured Composites" poster materials, Jun. 2001, Department of Materials Science and Engineering, University of Florida, Gordon Research Conference.

Sciadini, M.F. et al. "Evaluation of Bovine-Derived Bone Protein with a Natural Coral Carrier as a Bone-Graft Substitute in a Canine Segmental Defect Model" *J. Orthopaedic Res.*, 1997, 15:844-857.

Sivakumar, M. and K Panduranga Rao "Preparation, characterization and in vitro release of gentamicin from coralline hydroxyapatite-gelatin composite microspheres" *Biomaterials*, 2002, 23:3175-3181.

Tranquillo, R.T. et al. "Magnetically orientated tissue-equivalent tubes: application to a circumferentially orientated media-equivalent" *Biomaterials*, 1996, 17:349-357.

Traub, W. et al. "Origin of Mineral Crystal Growth in Collagen Fibrils" *Matrix*, 1992, 12:251-255.

Traub, W. et al. "Three-Dimensional Ordered Distribution of Crystals in Turkey Tendon Collagen Fibers" *PNAS USA*, Dec. 15, 1989, 86(24):9822-9826.

Weiner, S. et al. "Lamellar Bone: Structure-Function Relations" *J. Struc. Biol.*, 1999, 126:241-255.

Weiner, S. and W. Traub "Bone structure: from ångstroms to microns" *FASEB J.*, 1992, 6:879-885.

Weiner, S. and W. Traub "Organization of Crystals in Bone" in Mechanisms and Phylogeny of Mineralization in Biological Systems, Suga, S. and Nakahara, H., Eds., Chapter 2.21, pp. 247-253, 1991.

Zhang, R. and P. Ma "Poly(α-hydroxyl acids)/hydroxyapatite porous composites for bone-tissue engineering. I. Preparation and morphology" *J. Biomed. Mater. Res.*, 1999, 44:446-455.

Zund, G. et al. "Tissue engineering in cardiovascular surgery: MTT, a rapid and reliable quantitative method to assess the optimal human cell seeding on polymeric meshes" *Euro. J. Cardio-thoracic Surg.*, 1999, 15:519-524.

Kikuchi, M. et al. "Preparation of hydroxyapatite/collagen composites using biomimetic process and their biocompatibility" *Mat. Res. Soc. Symp. Proc.*, 2000, 599:51-53.

Roveri, N. et al. "Biologically inspired growth of hydroxyapatite nanocrystals inside self-assembled collagen fibers" *Mat. Sci. Eng.*, 2003, 23(3):441-446 (abstract).

Gower, L. "A model of biomineralization: Polymer-induced liquid-precursor (PILP) process" presented at Workshop on Investigation of Biomineralization Employing Model Systems, DFG Priority Programm 1117 Principles of Biomineralization, Braunschweig, Germany, Sep. 23-24, 2003.

Gower, L. et al. "The Influence of templates on mineralization via a precursor process" presented Aug. 12, 2002 at Gordon Research Conference (GRC), New London, New Hampshire.

Gower, L. et al. "Biomimetic bone" presented at ACERS 28th Int. Cocoa Beach Conference on Advanced Ceramics and Composites, Jan. 28, 2004, Cocoa Beach, FL.

Gower, L. "Biomimetic processing of ceramic composites" presented at CIMTEC-10th International Ceramics Congress and 3rd Forum on New Materials, Jul. 14-18, 2002, Florence, Italy.

Gower, L. "A new paradigm for biomineral formation" presented at 7th Int. Conf.—The Chemistry and Biology of Mineralized Tissues, Nov. 4-9, 2001, Sawgrass, FL.

Lee, I. et al. "Nanoparticle-directed crystallization of calcium carbonate" *Adv. Mater.*, 2001, 12(21):1617-1620.

Olszta, M.J. et al. "Synthesis of nano-fibrous $CaCO_3$ through a solution-precursor-solid (SPS) process" presented Apr. 7, 2003 at Materials Research Society (MRS) Spring Meeting, San Francisco, California.

Olszta, M.J. and L. Gower "Biomimetic composites using a polymer-induced liquid-precursor (PILP) process" presented Jun. 2002 at Annual Society for Experimental Mechanics (SEM) meeting, Milwaukee, Wisconsin.

Olszta, M.J. et al. "Scanning electron microscopic analysis of the mineralization of type I collagen via a polymer-induced liquid-precursor (PILP) process" *Calcif. Tissue Int.*, 2003, 72(5):583-591, Epub date Mar. 6, 2003.

Olszta, M.J. "Biomimetic mineralization of type-I collagen" presented at 7th Int. Conf.—The Chemistry and Biology of Mineralized Tissues, Nov. 4-9, 2001, Sawgrass, FL.

Olszta, M.J. et al. "Mimicking the nanostructured architecture of bone" presented at Fall Materials Research Society (MRS), Session L: Continuous Nanophase and Nanostructured Materials, Dec. 1-5, 2003, Boston, MA.

Olszta, M.J. "Biomimetic mineralization of type-I collagen" presented at UEF Biomimetic Engineering Conference, Mar. 3-7, 2002, Destin, FL.

Olszta, M.J. et al. "Biomimetic mineralization of type I collagenous matrices" presented at MRS Spring Meeting Proceedings, Symposium O-Materials Inspired by Biology, Apr. 21-25, 2003, San Francisco, CA.

METHOD FOR PRODUCING A MINERAL FIBER

CROSS-REFERENCE TO RELATED APPLICATIONS

This application is a continuation-in-part application of U.S. application Ser. No. 10/418,843, filed Apr. 18, 2003, which claims the benefit of U.S. Provisional Application No. 60/373,801, filed Apr. 18, 2002; and this application is a continuation-in-part application of U.S. application Ser. No. 10/691,002, filed Oct. 22, 2003; which are hereby incorporated by reference in their entirety, including all figures, tables, and drawings.

The subject invention was made with government support under a research project supported by the National Science Foundation Grant No. ECS-9986333. The government has certain rights in this invention.

BACKGROUND OF THE INVENTION

Synthetic bone graft material made to closely resemble natural bone would be a useful replacement for natural bone. Acceptable synthetic bone can avoid the problem of availability and harvesting of autogenous bone and the risks and complications associated with allograft bone, such as risks of infection, disease, and viral transmission.

Natural bone is a composite material consisting of both water and organic and inorganic solid phases. Bone has a hard structure because its organic extracellular collagenous matrix is impregnated with inorganic crystals, principally hydroxyapatite ($Ca_{10}(PO_4)_6(OH)_2$). Calcium and phosphate account for roughly 65% to 70% of the bone's dry weight. Collagen fibers compose approximately 95% of the extracellular matrix and account for 25% to 30% of the dry weight of bone. The organic material gives bone its flexibility and resilience, while the inorganic material gives bone its strength and rigidity (modulus), and the organization of the two phases provides a high degree of toughness to the composite. A thorough review of bone structure from the angstrom level (mineral crystal) to the micron level (lamellae) has been presented (Weiner, S. et al. [1992] *FASEB*, 6:879-885).

Surrounding the mineralized collagen fibers is a ground substance consisting of protein-polysaccharides, or glycosaminoglycans, primarily in the form of proteoglycan macromolecules. The glycosaminoglycans serve to cement together the various layers of mineralized collagen fibers. The individual collagen molecules self-assemble to form triple helices, which assemble into collagen fibrils, which then assemble into microscopic fibers. Within the packing of the collagen fibrils/fibers are distinct gaps, sometimes called hole zones. These hole zones are created by the staggered arrangement of tropocollagen molecules (triple helical rods), which leads to periodicity of the hole and overlap zones. Various models have been proposed where these hole zones are completely isolated from each other, or are contiguous and together form a groove. Within these hole zones, mineral crystals form. The mineral crystals in final form nucleate and grow within the fibrils (intrafibrillar mineralization), as well as into the interstitial spaces (interfibrillar mineralization) (Landis, W. J. et al. [1993] *J. Struc. Biol.* 110:39-54). The mineral crystals in final form are a carbonated apatite mineral (dahllite), but initially may form as an amorphous calcium phosphate phase, which then transforms into the apatite (or possibly via an octacalcium phosphate precursor, which naturally forms plates). The apatite platelets of bone are of nanoscopic dimensions (only a few unit cells thick), and are densely packed into the type I collagen fibrils due to the intrafibrillar mineralization mechanism, and are well oriented with their c-axis (in the [001] direction) parallel to the long axis of the collagen fibrils. Because of the nature of the packing, the orientation of the collagen fibrils will determine the orientation of the mineral crystals (Martin, R. B. et al. [1998] "Skeletal Tissue Mechanics", Springer-Verlag Publishers, New York, N.Y.).

There are numerous biocompatible artificial bone substitutes currently on the market. Of these substitutes, none successfully mimics the composite or microstructure of bone. For example, man-made ceramic composites have some of the desired properties of natural bone (such as matching of modulus), but are notoriously brittle and prone to cracking. By contrast, biological ceramics like bone and teeth resist cracking, with a high toughness and stiffness. It is the nanostructured architecture that leads to mechanical properties that are unique to bone, which are not readily duplicated by polymers (which are not strong or stiff enough), or ceramics (which are brittle and lack toughness, and usually not bioresorbable). These mechanical properties are important because of the body's natural repair processes, in which bone is a living tissue and the cells respond according to the stresses they sense in their surrounding tissue (according to Wolff's Law). If an implant material has too high of a modulus (stiffness), the cells tend to resorb the surrounding bone due to the phenomenon of stress shielding (the stiffer material carries more of the load than the surrounding bone).

A logical choice of materials for a synthetic bone substitute would be a collagen-hydroxyapatite composite; indeed, many have attempted to mineralize collagen in vitro, but the preparation of such a composite has been limited by the ability to achieve the high mineral loading that is attained biologically by intrafibrillar mineralization. An associated periodic contrast pattern is commonly observed by transmission electron microscopy (TEM) of collagen fibers (Carter, J. G. [1990] Skeletal Biomineralization: Patterns, Processes and Evolutionary Trends, Volume 1, Van Nostrand Reinhold Publishers, New York, N.Y.; Hodge, A. J. et al. [1963] "Recent studies with the electron microscope on ordered aggregates of the tropocollagen molecule", in Aspects of Protein Structure, Ramanchandran, G. N. (ed.), pp. 289-300, Academic Press, London, England; Katz, E. P. et al. [1989] *Connect. Tissue Res.*, 21:49-159). From tomographic imaging of naturally mineralizing turkey tendon (which is considered a model of secondary bone formation), there is evidence that the hydroxyapatite crystals first appear within the hole zones of collagen, and then spread throughout the fibrils, leading to the array of iso-oriented nanocrystals of highly organized hydroxyapatite [HAP] embedded within the organic matrix (Landis, W. J. et al. [1993] *Structural Biology*, 110:39-54; Landis, W. J. et al. [1991] *Connect. Tissue Res.*, 25:181-196). Alternatively, there has been evidence that the collagen fibers contain an amorphous substance during the early stages of bone formation, referred to by Bonnuci as an "inorganic substance in bands" (ISBs), which then crystallizes into the more commonly observed platy crystals (Bonnuci, E. *Calcification in Biological Systems* [1992] CRC Press Boca Raton, Fla.).

From a materials engineering perspective, the nanostructure of bone is intriguing and can be difficult to define. For example, it is not clear whether bone is more accurately characterized as a polymer-fiber-reinforced ceramic-matrix composite or a ceramic-nanoparticle-reinforced polymer-matrix composite. The two phases are so intimately linked that the mechanical properties are distinctly different than ceramics or polymers, and therefore are difficult to reproduce.

To date, scientists do not have a complete understanding of how bone is formed, even at this most basic level of structure. However, it is likely that the nanostructured architecture plays a role in the toughness of bone. Obviously, cellular control is important in biomineralization, and in the case of bone, helps to build its hierarchical structure (i.e., lamellae and osteons), but even the physicochemical mechanism for generating this nano-architecture has not been elucidated. Because intrafibrillar mineralization does not occur simply by attempting to crystallize collagen in vitro using supersaturated solutions of HAP (crystals only nucleate heterogeneously on the surface of the collagen fibers), it is generally assumed that nucleating proteins must be present within the gaps of the collagen fibrils.

It is understood within the biomineralization community that acidic proteins can act as inhibitors to crystal nucleation or growth (Addadi, L. et al. [1987] *Proc. Natl. Acad. Sci. USA*, 84:2732-2736; Addadi, L. et al. [1992] *Angew. Chem. Int. Ed. Engl.* 31:153-169; Mann, S. et al. [1983] *Structure and Bonding*, 54:125-174; Mann, S. et al. [1989] "Crystallochemical Strategies in Biomineralization" in Biomineralization-Chemical and Biochemical Perspectives. Mann, S., Webb, J., and Williams, R. J. P. (eds.), 33-62 (VCH Publishers, N.Y., N.Y.)). In the case of crystal growth, it has been shown that selective inhibition of growth along stereospecific crystallographic planes can lead to a change in crystal morphology (Addadi, L. et al. [1985] *Angew. Chem. Int. Ed. Engl.*, 24:466-485). In at least a few cases, acidic proteins have been shown to promote crystal nucleation (Addadi, L. et al. [1987] *Proc. Natl. Acad. Sci. USA*, 84:2732-2736; Greenfield, E. M. et al. [1984] *Amer. Zool.*, 24:925-932). It has also been shown that if the inhibitory action of a macromolecule is not complete, certain conditions lead to the induction (stabilization) of an amorphous liquid-phase precursor (Gower, L. B. et al. [2000] *J. Crystal Growth*, 210(4):719-734), which can have a profound consequence on crystal morphology since transformation of an amorphous precursor does not proceed via the same mechanism as traditional solution crystal growth (Mann, S. et al. [1989] "Crystallochemical Strategies in Biomineralization" in Biomineralization-Chemical and Biochemical Perspectives. Mann, S., Webb, J., and Williams, R. J. P. (eds.), 33-62 (VCH Publishers, N.Y., N.Y.)). Certain features of this polymer-induced liquid-precursor (PILP) process suggest that this mechanism may occur during morphogenesis of calcium carbonate biominerals in invertebrates (Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119).

The present inventors have demonstrated that when the PILP phase is deposited onto an amorphous glass substrate, continuous thin films (~500 nm thick) of $CaCO_3$ are formed (Gower L. A. et al., "Deposition of Calcium Carbonate Films by a Polymer-Induced Liquid-Precursor (PILP) Process" *Journal of Crystal Growth*, 2000, 210(4):719-734). Organic substrates, such as type-I collagen, have also been used as substrates on which to deposit the PILP phase, resulting in intrafibrillarly mineralized organic/mineral composites (Olszta M. J. et al., [2003] *Connective Tissue Research*, 44:326-334; Olszta, M. J. et al., [2003] *Calcified Tissue International*, 72(5): 583-591). Neither of the previous substrates used were of a crystalline nature and, therefore, epitaxial interaction within the crystallization mechanism was not possible.

BRIEF SUMMARY OF THE INVENTION

The subject invention concerns a mineral fiber that is useful as a biomimetic substitute for bone and other tissues, such as dental enamel, and as filler in paper, paint, coatings, and plastics production. The mineral fiber of the present invention comprises a fibrous mineral phase having a high aspect ratio. The present invention also provides in vitro methods for making the mineral fibers, methods of using the mineral fibers to treat tissue defects, and compositions comprising the mineral fibers.

In one embodiment, the method for producing the mineral fiber comprises contacting an inorganic liquid-phase mineral precursor with a crystalline inorganic substrate under conditions permitting the inorganic liquid-phase mineral precursor to solidify and crystallize, thereby forming the mineral fiber. Preferably, the formed mineral fiber exhibits a single crystalline birefringence and a single crystalline electron diffraction pattern. The crystalline inorganic substrate can comprise any of a variety of minerals, such as calcite rhombs or hydroxyapatite. The mineral can be nucleated on a solid surface. The crystalline inorganic substrate can comprise other mineral compositions suitable for stimulating calcite nucleation from the PILP "flux" droplet. The inorganic liquid-phase mineral precursor preferably comprises an inorganic mineral this is generated by a liquid-phase amorphous-mineral precursor that can be formed by contacting an acid polymer with a mineralizing solution under conditions permitting formation of the inorganic liquid-phase mineral precursor.

Preferably, the acidic polymer contacted with the mineralizing solution comprises at least one member selected from the group consisting of polyacrylic acid, polymethacrylic acid, sulfonated polymer, phosphorylated proteins or peptides, phosphorylated synthetic polymers, sulfated polysaccharides, sulfated glycoproteins, polyaspartic acid, polyglutamic acid, polyaspartate, polyvinyl phosphate, and polyvinyl phosphonate, or combinations of any of the foregoing.

Preferably, the inorganic liquid-phase mineral precursor comprises at least one member selected from the group consisting of calcium phosphate, calcium carbonate, hydroxyapatite, strontium carbonate, barium carbonate, and calcium sulfate, strontium sulfate, calcium oxalate, magnesium-bearing calcium carbonate, and magnesium-bearing calcium phosphate. In other embodiments, the inorganic liquid-phase mineral precursor comprises at least one member selected from the group consisting of hydroxyapatite, octacalcium phosphate, tricalcium phosphate, carbonated hydroxyapatite, fluorinated hydroxyapatite, brushite, magnesium containing hydroxyapatite, dicalcium phosphate dihydrate, and amorphous calcium phosphate.

Biologically active agents can be associated with the fibers of the present invention. For example, the biologically active agent can comprise at least one member selected from the group consisting of medicaments; vitamins; mineral supplements; substances used for the treatment, prevention, diagnosis, cure or mitigation of disease or illness; substances affecting the structure or function of the body; drugs; antimicrobial agents; antifungal agents; antibacterial agents; antiviral agents; antiparasitic agents; growth factors; angiogenic factors; anaesthetics; mucopolysaccharides; metals; cells; acid mucopolysaccharides; proteins; enzymes, peptides; and wound healing agents.

In one embodiment, the fiber forming method further comprises forming the inorganic liquid-phase mineral precursor by combining calcium salt and an acidic polymer to form an aqueous solution, and reacting the aqueous solution with ammonium carbonate vapor or ammonium phosphate vapor. Optionally, the aqueous solution is reacted with the ammonium carbonate vapor, and the ammonium carbonate vapor is provided through the decomposition of at least one ammonium carbonate material selected from the group consisting of ammonium carbonate monohydrate, ammonium carbonate dihydrate, and ammonium carbamate. In other embodiments, the aqueous solution is reacted with the ammonium phosphate vapor, and the ammonium phosphate vapor is provided through the decomposition of at least one ammonium phosphate material selected from the group consisting of ammonium phosphate monobasic, ammonium phosphate dibasic.

The fiber forming method can further involve forming the inorganic liquid-phase mineral precursor by combining calcium chloride and a combination of acidic polymers to form an aqueous solution, and reacting the aqueous solution with ammonium phosphate vapor or with a phosphate containing solution. In other embodiments, the method involves forming the inorganic liquid-phase mineral precursor by combining calcium salt and a combination of acidic polymers to form an aqueous solution, and reacting said aqueous solution with phosphate generated by enzymatic degradation of phosphate containing compounds. In other embodiments, the method involves forming the inorganic liquid-phase mineral precursor by combining calcium salt and ammonium phosphate, and a combination of acidic polymers to form an aqueous solution, in which precipitation is caused by at least one of the following conditions: a change of temperature, a change of pH, evaporation, or removal of crystallization inhibitor.

The inorganic liquid-phase mineral precursor can be contacted with the crystalline inorganic substrate under various conditions. Preferably, the inorganic liquid-phase mineral precursor is contacted with the crystalline inorganic substrate in an aqueous solution at a temperature of 4° C. or higher. In preferred embodiments, the contacting of the inorganic liquid-phase mineral precursor with the crystalline inorganic substrate involves contacting droplets of the inorganic liquid-phase mineral precursor with the crystalline inorganic substrate, wherein the droplets coalesce and solidify, and wherein the inorganic fiber is formed outward from the interface of the droplets and the crystalline inorganic substrate. The droplets of inorganic liquid-phase mineral precursor include primary droplets that contact the crystalline inorganic substrate and secondary droplets that contact the primary droplets, wherein the secondary droplets extend the length of the inorganic fiber. Preferably, the secondary droplets extend the length of the inorganic fiber in a continuous fashion as a PILP phase is continuously generated through constant composition or batch replenishment techniques. Using the method of the invention, the inorganic liquid-phase mineral precursor can crystallize in an epitaxial orientation.

In one embodiment, the inorganic liquid-phase mineral precursor comprises hydroxyapatite and the inorganic crystalline substrate comprises a hydroxyapatite film.

Typically, the mineral fibers formed using the methods of the present invention have a high aspect ratio (length to diameter) in the range of about 5 (5:1) to 60 (60:1). In some embodiments, the fiber aspect ratio will be in the range of about 10 (10:1) to 60 (60:1). The formed fiber also has a mineral phase that is homogenously distributed throughout the width (cross-section) of the fiber (i.e., not a hollow cylinder). Typically, the mineral fibers formed have a diameter within the range of about 100 nm to 2 μm. Small individual fibers can be grown together in the same direction, thereby forming a fiber bundle of larger diameter (e.g., 100 nm to 1 mm). In some embodiments, the mineral fiber of the present invention does not comprise a metal.

BRIEF DESCRIPTION OF THE DRAWINGS

In FIG. 1A, the polymer-induced liquid-precursor (PILP) phase is separated from solution in the form of nm-μm diameter droplets 10 of PILP phase. In FIG. 1B, these droplets then physisorb onto an existing crystalline (e.g., calcite) surface 20 and either solidify (● denoted by closed circle) or remain liquid (○ denoted as an open circle). In FIG. 1C, subsequent droplets 10 that contact a solid primary droplet wick to the surface and form a film 30 surrounding the solid droplet. Secondary droplets that contact the primary liquid droplet coalesce with it. As subsequent droplets coalesce, primary droplets solidify, therefore pushing the fiber 40 away from the calcite surface (arrow denotes growth direction). In FIG. 1D, fiber growth continues as long as the liquid "bobble" 50 on the fiber head remains a liquid, continually forcing the fiber 40 away from the calcite surface (arrow denoted growth direction).

DETAILED DESCRIPTION OF THE INVENTION

The present invention pertains to mineral fibers and in vitro methods for producing mineral fibers utilizing an inorganic liquid-phase mineral precursor (PILP). According to the fiber forming method of the present invention, the PILP is contacted with a crystalline inorganic substrate under conditions permitting the PILP to solidify, crystallize, and extend away from the crystalline substrate, thereby forming the mineral fiber.

According to the fiber forming methods of the present invention, the mineral fibers typically grow or extend in a substantially unidirectional manner, away from the crystalline substrate (thereby forming substantially linear mineral fibers). When there are fluctuations in the reaction, such as the temperature of the crystallizing solution, the fibers appear to grow in a serpentine manner, much like the serpentine growth exhibited by the fibers produced by the vapor-liquid-solid (VLS) mechanism or solution-liquid-solid (SLS) mechanism when the temperature is varied, as described by Trentler T. J. et al. (Trentler, T. J. et al. [1995] *Science*, 270(5243):1791-1794; Wagner, R. S. and W. C. Ellis, [1964] *Applied Physics Letters*, 4(5):89; Wagner, R. S. and W. C. Ellis, [1964] *Journal of Metals*, 16(9):761).

The inorganic liquid-phase mineral precursor utilized to form mineral fibers of the present invention can be produced using a variety of methods. For example, synthesis of a liquid-phase precursor of calcium carbonate has been described previously (Gower, L. B. and D. J. Odom [2000] J. Crystal Growth 210(4):719-734; Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119; Gower, L. A. and D. A. Tirrell [1998] J. Crystal Growth 191(1-2):153-160), where vapor diffusion of the decomposition products of crushed ammonium carbonate $(NH_4)_2CO_3$ into a solution containing calcium chloride $(CaCl_2)$ is used to slowly raise the supersaturation of calcium carbonate; and one or more short-chain acidic polymer additives is added to induce the precursor mechanism. Alternative methods can be used to gradually raise the supersaturation of the crystallizing solution, including direct addition of a carbonate containing solution to the calcium containing solution; or the escape of carbon dioxide gas from a saturated calcium bicarbonate solution (which is produced by bubbling carbon dioxide into an aqueous solution containing the calcium carbonate salt). Supersaturation can also be raised using temperature, pH, or removal of inhibitory species. Similar methods can be used for the calcium phosphate system, although higher temperature (37° C.) is more favorable for decomposition of ammonium phosphate (or any derivations of ammonium phosphate, such as ammonium phosphate dibasic). The phosphate counterion can be produced using enzymes that cleave phosphate-containing moieties, or through the degradation of phosphate containing phospholipid vesicles such as seen in Murphy and Messersmith (W. L. Murphy, P. B. Messersmith, Compartmental control of mineral formation: adaptation of a biomineralization strategy for biomedical use. *Polyhedron* 19, 357 (2000)). According to the fiber formation method of the present invention, the crystalline substrate can then be contacted with the liquid-phase precursor of the inorganic mineral, such as calcium phosphate, calcium carbonate, hydroxyapatite, strontium carbonate, calcium sulfate, calcium oxalate, calcium oxide, magnesium-bearing calcium carbonate or phosphate, or any polymorphs of these minerals.

The crystalline inorganic substrate used in the fiber forming method permits epitaxial interaction within the crystallization mechanism. The crystalline substrate can comprise any of a variety of minerals, such as calcite rhombs or hydroxyapatite. It is not necessary that the crystalline substrate be a solid crystal. For example, the crystalline substrate can be a mineral thin film. For example, thin films comprising one or more of $CaCO_3$, $CaPO_4$, $BaCO_3$, and $SrCO_3$ can be used. Preferably, the thin film is a patterned thin film, which allows control of fiber location.

One or more of a variety of acidic polymers, such as acidic short-chained polymers, can be utilized to initiate the amorphous liquid-phase mineral precursor, including different polymers and biological materials. Polyacrylic acid (PAA), polymethacrylates (PMA), sulfonated polymers, phosphorylated proteins, peptides and polymers, sulfated glycoproteins, polyaspartic acid, polyglutamic acid, polyaspartate, polyvinyl phosphate, and blends or copolymers of these materials, individually and in mixtures, can be utilized to induce the liquid-phase separation, for example. A range of polymer molecular weights can be suitable if the other variables of the crystallizing conditions are appropriately modified to generate the PILP phase. Preferably, molecular weights in the range of 2,000 to 15,000 g/mol enhance the ability to induce formation of the precursor.

The methods of the subject invention can be carried out under a variety of conditions. For example, in the case of an aqueous system, the fiber forming method can be carried out at a temperature of about 0° C. to about 100° C. Preferably, the method is carried out at about 4° C. or higher. More preferably, the method is carried out at about 37° C., to match physiological conditions. The method can be carried out at a pH in the range of about 5 to about 10. Preferably, the method is carried out at a pH of about 7.0 to about 7.8 and 1 atm. More preferably, the method is carried out at a pH of about 7.4.

The type of reaction vessel or vessels utilized for producing the mineral fibers of the present invention, or their sizes, are not critical. Any vessel or substrate capable of holding or supporting the PILP and/or crystalline substrate so as to allow the reaction to take place can be used. Preferably, the supersaturation is gradually increased, allowing time for the acidic polymer to induce and stabilize the liquid-phase mineral precursor. It should be understood that, unless expressly indicated to the contrary, the terms "adding", "contacting", "mixing", "reacting", "combining" and grammatical variations thereof, are used interchangeable to refer to the mixture of reactants of the process of the present invention (e.g., acidic polymer additives, calcium-containing solution, and so forth), and the reciprocal mixture of those reactants, one with the other (i.e., vice-versa).

The mineral fibers formed using the methods of the present invention typically have a high aspect ratio (length to diameter) in the range of about 5 (5:1) to 60 (60:1). In some embodiments, the fiber aspect ratio will be in the range of about 10 (10:1) to 60 (60:1). The formed fiber has a mineral phase that is homogenously distributed throughout the width (cross-section) of the fiber (i.e., not a hollow cylinder). Typically, the mineral fibers formed have a diameter within the range of about 100 nm to 2 μm. Small individual fibers can be grown together in the same direction, thereby forming a fiber bundle having a larger diameter (e.g., 100 nm to 1 mm). In some embodiments, the mineral fiber of the present invention does not comprise a metal.

The present invention further concerns a method of treating a patient having a tissue defect by applying mineral fibers of the subject invention (and compositions comprising the fibers) to the site of the tissue defect. As used herein, the term "patient" refers to any human or non-human animal suffering from a tissue defect. According to the method of the subject invention, a therapeutically effective amount of the fibers or composition can be applied at the site of a tissue defect to partially or fully restore structural integrity to the tissue. Once applied, the mineral fibers of the subject invention can function as a filler (or partial filler) or plug, to mend the tissue defect. The amount to be applied will depend upon the size and nature of the tissue defect, and the clinical outcome that is sought. The fibers can be applied within a composition in a malleable form, for example, as a paste or putty, such that the administered composition takes the shape of the bone defect. Alternatively, the composition can be molded pre-cast into a desired shape (such as the shape of the defect) using polymer composition molding methods known to those of ordinary skill in the art, and the molded composition can be administered as a solid or semi-solid article. Thus, the size, volume, thickness, and shape of the molded article can be controlled, as desired. The composition can be applied in particulate form. According to the method of the subject invention, the mineral fibers can be applied so that they directly contact existing tissue adjacent to, or defining, the tissue defect site, or the mineral fibers can be contacting another implant, or both.

The composition of the subject invention (also referred to herein as constructs or fiber constructs or fibrous constructs) can be applied to the tissue defect site as a liquid. Once applied, with a syringe for example, the liquid composition can coagulate or cure ("set") shortly after application to form a solid.

The mineral fibers of the subject invention (and compositions comprising the fibers) can be used as a vehicle for the in situ delivery of biologically active agents. The biologically active agents incorporated into, or included as an additive within, the fibers of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the mineral fibers into a patient and to promote subsequent integration and healing processes. The active agents include, but are not limited to, antifungal agents, antibacterial agents, anti-viral agents, anti-parasitic agents, growth factors, angiogenic factors, anaesthetics, mucopolysaccharides, metals, cells, and other wound healing agents. Because the processing conditions can be relatively benign (physiological temperature and pH), live cells can be incorporated into fiber constructs during their formation, or subsequently allowed to infiltrate the fibers or compositions through tissue engineering techniques.

As indicated above, cells can be seeded onto and/or within the mineral fiber constructs of the present invention. Likewise, tissues such as cartilage can be associated with the mineral fibers prior to implantation within a patient. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogenic. Seeded cells can be encapsulated or non-encapsulated.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into the fibers and compositions of the present invention include, but are not limited to, bone growth factors (e.g., BMP, OP-1) basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-α and TGF-β), interleukin-8 (IL-8), granulocyte-macrophage colony stimulating factor (GM-CSF), the interleukins, and the interferons.

Other agents that can be incorporated into the fibers or compositions of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that can be incorporated into, or included as an additive within, the fibers or compositions of the subject invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, enzymes, or combinations and biologically active fragments thereof. Other proteins associated with other parts of human or other mammalian anatomy can be incorporated or included as an additive, including proteins associated with cartilage, such as chondrocalcining protein, proteins associated with dentin, such as phosphoryin, glycoproteins and other Gla proteins, or proteins associated with enamel, such as amelogenin and enamelin. Agents incorporated into the fibers or compositions of the subject invention may or may not facilitate or enhance osteoinduction. Adjuvants that diminish an immune response can also be used in conjunction with the fibers or compositions of the subject invention.

The biologically active agents can first be encapsulated into microcapsules, microspheres, microparticles, microfibers, reinforcing fibers and the like to facilitate mixing and achieving controlled, extended, delayed and/or sustained release. Encapsulating the biologically active agent can also protect the agent against degradation during formation of the fibers or compositions of the invention.

Additionally, the biologically active agents can be pendantly attached to the PILP phase or the formed fibers. The attachment can be facilitated through covalently linking the agent to inorganic phase, or through the use of hydrogen bonding.

In preferred embodiments of the invention, the biologically active agent is controllably released into a mammal when the fibers or composition of the invention is implanted into a mammal, either through degradation in the aqueous environment, or more preferably, due to bioresorption relying on the time scale resulting from cellular remodeling. The fibers or fibrous constructs of the subject invention can be used to replace an area of discontinuity in the tissue in the mammalian body. The area of discontinuity in the tissue can be as a result of trauma, disease, genetic defect, tumor, or surgery, for example.

The compositions of the subject invention can be formulated into a variety of shapes suitable for its function as a tissue implant, such as a plate, pin, rod, screw, anchor, tack, arrow, staple, button, or other regular or irregular shape. The composition of the present invention can be formulated as a three-dimensional scaffold and, optionally, seeded with one or more cell types for implantation within a patient. For example, a hydroxyapatite (HAP) containing PILP can be used to produce fibrous HAP for dental applications. Teeth are composed of various biomineral layers, with the enamel layer being composed of fibrous HAP. Using the mineral fiber forming method of the present invention, the HAP containing PILP can be deposited onto HAP films to produce an ordered array of fibrous crystals for dental applications.

The term "tissue defect", as used herein refers to any tissue deficient region, such as a void, gap, recess, or other discontinuity in the hard or soft tissues. The tissue defect can be artificially or naturally established, and can occur due to disease or trauma, for example. Thus, the tissue defect can occur as a consequence of pathologic, inflammatory, or tumor diseases, surgical interventions, congenital defects, or bone fractures, and the like. Typically, tissue defects in dental applications will be on or within the gum or jaw of the patient's mouth. For example, in the case of certain diseases, such as tumors, the tissue defect is artificially established by removing the tumor tissue. Thus, according to the method of the subject invention, the mineral fibers or compositions containing the mineral fibers can be applied, for example, to repair periodontal defects, for craniofacial reconstruction, joint reconstruction, fracture repair, to conduct orthopedic surgical procedures, and spinal fusion, for example. The term "tissue defect" is also intended to include anatomical sites where augmentation to a tissue feature is desired by the patient in the absence of disease or trauma, such as in elective cosmetic surgery. Thus, the "defect" can be one that is subjectively perceived by the patient, and where augmentation of the bone deficient region is desired.

The term "polymorph", as used herein, refers to inorganic minerals that are similar in chemical composition but have different crystal structures.

The terms "comprising", "consisting of", and "consisting essentially of" are defined according to their standard meaning and may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a fiber" includes more than one such fiber, and the like. Reference to "an acidic polymer" includes more than one such polymer, and the like.

In addition to their therapeutic applications, the mineral fibers of the present invention may be used as filler in plastics, paint, coatings, and paper production. For example, calcium carbonate is used in a wide range of plastics as a filler, most notably PVC piping. Calcium carbonate fibers of the present invention are particularly useful in these applications because they have high aspect ratios that enhance reinforcement (modulus and strength), and their small size provide excellent surface area for adhesion to the matrix phase. In addition, calcite has a Moh's hardness of 3. In contrast, aragonite, which naturally forms needlelike crystals and is currently the only "fibrous" calcium carbonate available for filler, has a Moh's hardness of 4, making it slightly harder than calcite. Thus, using a fibrous calcite mineral phase would result in less wear on machinery. In addition, unlike the fibers of the present invention, the needle-like shape of aragonite crystals are not in the form of individual fibers, but are packed within spherulitic bundles which are not readily separated as isolated fibers for manipulation into the above composites.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

Materials and Methods

Polymer-Induced Liquid-Precursor (PILP) Process. The preparation of a PILP phase has been described previously (Gower, L. B. and D. J. Odom [2000] *J. Crystal Growth*, 210(4):719-734; Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119; Gower, L. A. and D. A. Tirrell [1998] *J. Crystal Growth*, 191(1-2):153-160). The general process introduces the acidic polymer into an aqueous salt solution which is slowly raised in supersaturation. One common method for raising supersaturation is to slowly introduce one of the ionic species, for example using a modified vapor diffusion technique developed by Addadi et al. (Addadi, L. et al. [1985] *Proc. Natl. Acad. Sci. USA*, 82:4110-4114), in which ammonium carbonate $(NH_4)_2CO_3$ vapor, produced by decomposition of its powder, diffuses into a solution containing calcium chloride $CaCl_2$ and the acidic polymeric additive. This multistage process is illustrated by the formula:

Stage I
Precursor Deposition

Stage II
Precursor Transformation

Alternatively, calcium phosphate (CaP) readily forms an amorphous gel prior to crystallization, which may be contacted with the inorganic crystalline substrate.

Typically, the crystal products are deposited onto a thin glass coverslip (22 mm D.) that is placed in the crystallizing solution, which can then be examined by polarized light microscopy (including in situ examination with ultra-long-working-distance objectives), or gold coated for scanning electron microscopy (SEM). The exact concentration of the reactants can vary.

Formation of Inorganic Crystalline Substrate. Substrate crystals were synthesized in two different manners, which provided calcite crystals of typical rhombohedral habit, but which differed in size and defect texture. For the first set of experiments, micron sized calcite rhombs (20-40 µm) were deposited on glass slides via a vapor diffusion method (Addadi, L., Moradian, J., Shay, E., Maroudas, N. G. and Weiner, S., *Proc. Natl. Acad. Sci. U.S.A.* 1987, 84, 2732-2736). For comparison, larger, millimeter sized calcite rhombs were grown through a metasilicate gel method. For the first type, glass substrates (22 mm diameter microscope coverslips) were placed into small petri dishes containing 3 ml of a 24 mM $CaCl_2.H_2O$ (Sigma) solution, and this crystallizing solution was placed in an enclosed chamber (e.g. a desiccator) containing small vials of freshly crushed ammonium carbonate. The carbonate powder decomposes into a vapor ($CO_2$ and $NH_3$) at room temperature, which slowly diffuses into the calcium solution, providing a means for gradually raising the supersaturation of $CaCO_3$. The larger 0.5 mm calcite crystals were fabricated in a gel medium through a controlled chemical reaction method. A sodium metasilicate gel was prepared using 0.5 M $CaCl_2.H_2O$ (Sigma) in a 0.35 M $Na_2O_3Si.9H_2O$ (Sigma) solution, which was allowed to set in 15 mm dia/127 mm long glass test tubes overnight until gelation. Subsequently, 0.1 M ammonium carbonate solution was added to each test tube and then covered with parafilm. The ammonium carbonate was allowed to diffuse into the gel over a period of 1 month, at which time large calcite crystals were gently removed with tweezers and rinsed several times with deionized water. The larger calcite crystals were analyzed using EDS in order to assure no Si remained on the surface of the crystals. A third manner to make calcite surfaces, tailored to have specific surface density characteristics, can be made following Teng (H. H. Teng, Controls by saturation state on etch pit formation during calcite dissolution. *Geochimica Et Cosmochimica Acta* 68, 253 (January, 2004)). Briefly, Teng found that by cleaving a large optical-quality Iceland spar (calcite) with a razor blade, to expose the {10-14} face, he could study the surface dissolution kinetics via the addition of solutions undersaturated with respect to $CaCO_3$. He concluded that when the saturation index $\Omega>0.541$ ($\Omega$ is defined as the ratio of ionic activity product to solubility product), no etch pit formation was observed, and dissolution occurred at existing steps. When $\Omega$ was decreased to 0.541-0.410, pits began to appear and with continuous decrease in saturation allowed for pit density to increase with continued dissolution at step edges. Finally, when $\Omega$ was lowered below ~0.007, there was a sharp increase in pit density.

These observations suggest that the defect texture of calcite crystals can be easily controlled, thereby increasing the fiber density. An alternative means for controlling defect texture is to introduce impurities into the crystals during their formation, such as other inorganic ions or molecular compounds, including polymeric additives.

Formation of Fibrous Crystals. The substrate crystals were introduced into the crystallizing system by placing the glass coverslips which had nucleated the 20-40 μm calcite rhombs (or contained 3 to 4 of the larger gel grown rhombs) in the bottom of a small petri dish filled with 3 ml of a 12 mM calcium chloride dihydrate solution, containing 0.24 mM $MgCl_2.6H_2O$ or $SrCl_2.6H_2O$, along with 200 μg/mL of polyacrylic acid (5,100 M. W., Sigma) to induce the PILP process (Gower, L. B. and Odom, D. J. J. Crystal Growth, 2000, 210:719-734). The $Mg^{2+}$ and $Sr^{2+}$, which are routinely found in naturally occurring calcite morphologies, were added because we have determined that they enhance the PILP process (inhibit solution crystal nucleation). $CO_2(g)$ was delivered to the sample solutions via the decomposition of crushed ammonium carbonate powder in the same manner as described above for synthesizing substrate crystals. Each of the sample solutions and ammonium carbonate vials were covered with parafilm, into which small holes were punched in order to slowly raise the supersaturation of the calcium carbonate in solution. All components of the reaction were then placed in an enclosed chamber, which allowed diffusion of the carbonate into the solution. Control experiments, containing no polymer, were performed alongside each experiment. For further characterization, the coverslips containing the small rhomb substrate crystals (or individual large gel-grown calcite rhombs) were carefully removed from solution with tweezers and rinsed with ultrapure $H_2O$ and then with ethanol (by gently dipping coverslip in a rinse beaker to avoid dislodging the fragile fibers) in order to remove any soluble salts. The glass slides were then examined using an Olympus BX-60 optical microscope in transmission mode, using crossed polars and an optional first-order-red wave plate.

Polarized Optical Light Microscopy (POM) Analysis. Samples were examined on the glass slides in transmission mode using an Olympus BX60 polarized optical microscope with first-order red wave-plate. The wave-plate allows one to observe both amorphous and crystalline phases, which is quite useful for examining crystallization reactions that proceed via precursor mechanisms. In this case, it was also useful for examining the crystallographic orientation of the fibers. Under plane polarized light (PPL), a crystal will appear dark (extinct) under crossed polars when its vibration directions are oriented parallel to one of the polars (indicated as "p" and "a" for polarizer and analyzer direction, respectively). When a gypsum plate is inserted, the crystal in the extinct position will exhibit the same retardation color as the magenta background. Maximum birefringence will occur when the crystal is rotated 45° from the analyzer and polarizer due to constructive interference of the light waves. Calcite is an optically negative material, therefore when the slow vibration direction of the wave-plate (indicated as "sd" double arrow) is parallel with the slow axis of the calcite (indicated by short arrow in NE corner), the combined vibrations will destructively interfere and the fiber will appear blue (a fall in interference color determined from Michel Levy chart). Conversely, the yellow color in the opposite quadrants indicates the slow ray of the crystal is parallel to the slow direction of the accessory plate. This type of analysis allows one to identify if there is a uniform orientation of the crystallographic axes within irregular shaped crystals, such as the fibers described here.

Scanning Electron Microscopy (SEM) Analysis. The samples were dried overnight, fixed to an aluminum stub using carbon paste or double-sided copper tape and then Au/Pd coated. The samples were then examined with either a JEOL 6400 SEM or a JEOL 6335F FEGSEM instrument, both equipped with energy dispersive spectrometers (EDS), at an accelerating voltage of 15 kV.

Transmission Electron Microscopy (TEM) Analysis. In order to examine the fibrous calcium carbonate, the samples were first scratched with a razor blade to dislodge some of the fibers from the rhomb substrate. A small aliquot of ethanol was then dispensed onto the scratched area and immediately drawn up using a micropipette. The removed aliquot was then dropped onto a 200 mesh copper TEM grid coated with thin layers of Formvar and amorphous carbon. The grid was air-dried and subsequently sputter coated with amorphous carbon for stability. The sample was examined on a JEOL 200cx transmission electron microscope at 200 kV in brightfield (BF) and selected area diffraction (SAD) modes.

EXAMPLE 1

Calcium Carbonate Fibers

Fibrous calcium carbonate ($CaCO_3$/calcite) crystals 100-800 nm in diameter were produced at temperatures as low as 4° C. The calcium carbonate fibers were deposited onto calcite rhombs using a mineralization process involving the inclusion of short-chained acidic polymers (e.g., polyaspartic acid or polyacrylic acid) to a supersaturated calcium carbonate system to induce an amorphous liquid-phase precursor. This latter process, documented in the literature, is known as the polymer-induced liquid-precursor (PILP) process. In previous reports, the present inventors have demonstrated that when the PILP phase is deposited onto an amorphous glass substrate, continuous thin films (~500 nm thick) of $CaCO_3$ are formed (Gower, L. B. and D. J. Odom [2000] *J. Cryst. Grow.*, 210(4):719-734). Organic substrates, such as type-I collagen, have also been used on which to deposit the PILP phase, resulting in intrafibrillarly mineralized organic/mineral composites (Olszta, M. J. et al., [2003] *Conn. Tiss. Res.*, 44:326-334; Olszta, M. J. et al., [2003] *Calcified Tissue International*, 72(5):583-591). Because these substrates were not of a crystalline nature, there was no possible epitaxial interaction involved in the crystallization mechanism.

In the present experiment, crystalline substrates were used which were synthesized by nucleating 20-40 μm calcite rhombs onto glass substrates. When no polymer was used to induce the PILP process, epitaxial overgrowth of calcite roughened the surface of the existing calcite seeds. $CaCO_3$ PILP droplets preferentially deposited onto the calcite rhombs instead of the glass, but did not form completely continuous films on the faces of the calcite. On a majority of the rhombs, fibrous crystals, which exhibited a single crystalline birefringence, were observed growing from each of the faces. The fibrous crystals were identified as calcite using electron diffraction, and although the diffraction patterns were single crystalline in nature, brightfield (BF) transmission electron microscopy (TEM) images of the majority of fibers showed distinct grains, suggesting that they are polycrystalline with all of the grains aligned in the same orientation. Scanning electron microscopy (SEM) confirmed this polycrystalline nature, as the surface of the fibers appear to be covered in iso-oriented calcite rhombs. It is also possible that these features are microfacets arising from surface reorganization of the energetically unfavorable curved crystals surfaces. In addition, using SEM, enlarged bobbles were observed on the growing ends of the fibers.

The observation of single crystalline fibers growing off of the crystalline inorganic substrates, in combination with the enlarged bobbles at the ends of the fibers, indicates that the process may bear some similarity to existing high temperature crystal growth mechanisms, such as the vapor-liquid-solid (VLS) and solution-liquid-solid (SLS), used to produce nanofibrous semiconductor materials. These processes function through the use of a metal nuclei, which is heated above its melting temperature and placed in an appropriate atmosphere (once the metal has melted, it is referred to as a flux). In the VLS mechanism, a high melting temperature metal is set on a silicon substrate and placed in a vapor atmosphere, whereas in the SLS, a low melting temperature metal is placed in an organometallic solution. Once these metals melt (creating the flux droplet), crystallizing constituents in the atmosphere (vapor or liquid) begin to diffuse into the flux. As a supersaturation of these constituents is reached, crystallization occurs either on the solid surface (VLS) with epitaxial orientation, or with the lowest energy plane forming (SLS) at the flux wall. As long as the temperature is kept above the melting temperature of the metal flux, and the concentration of the crystallizing constituent within the flux droplet is kept constant, the fibers continue to grow, restricted to one dimensional growth by the dimension of the flux droplet containing the reactants.

Figure 1A:
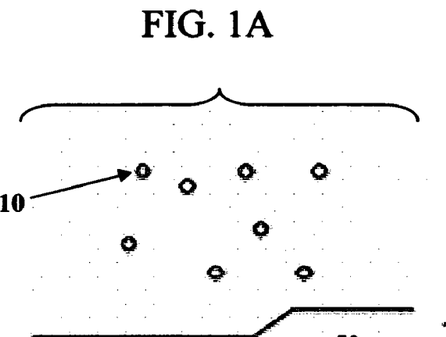
FIGS. 1A-1D show a schematic representation of mineral fiber formation according to a method of the present invention.
Figure 1B:
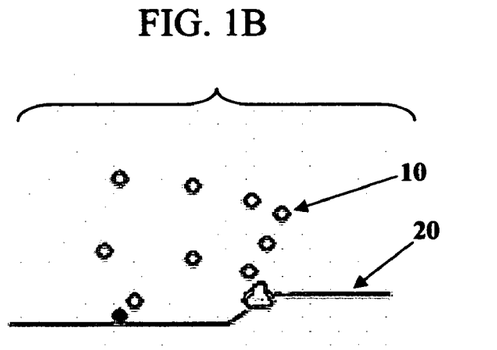
Figure 1C:
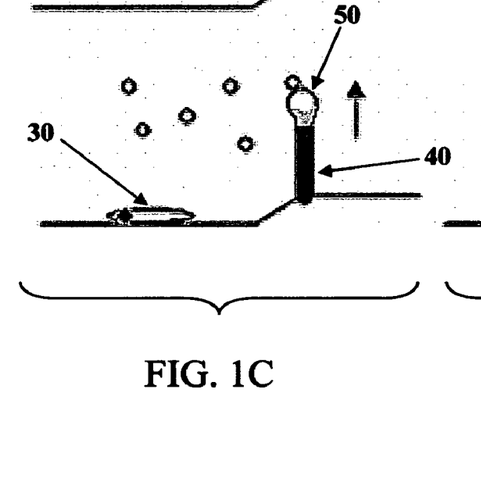
Figure 1D:
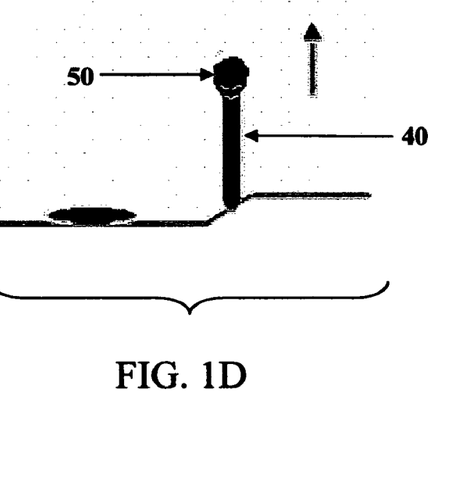
Figure 2A:
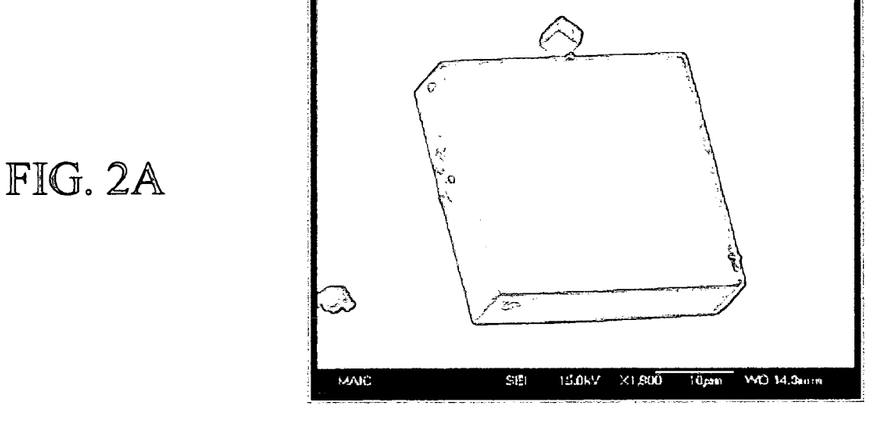
FIGS. 2A-2C show micrographs demonstrating, respectively, classical calcite nucleation, thin films deposited via a polymer-induced liquid-precursor (PILP), and calcite overgrowth on calcite via traditional solution growth (in the absence of the PILP phase).
Figure 2B:
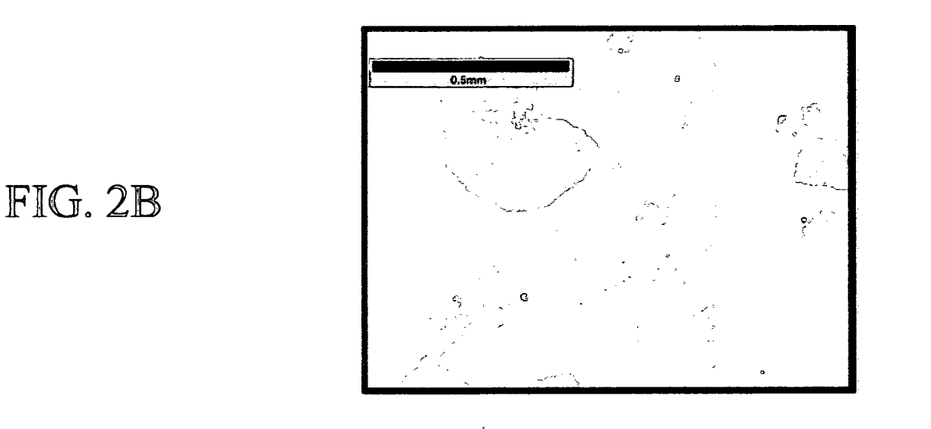
Figure 2C:
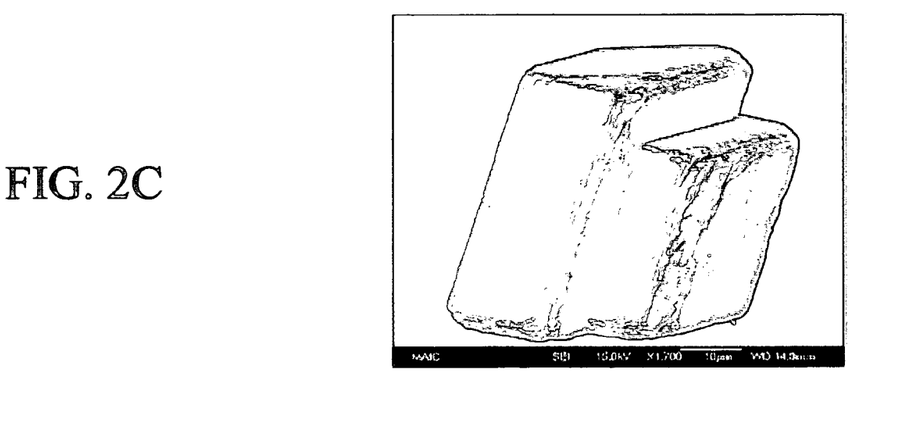
Figure 3A:
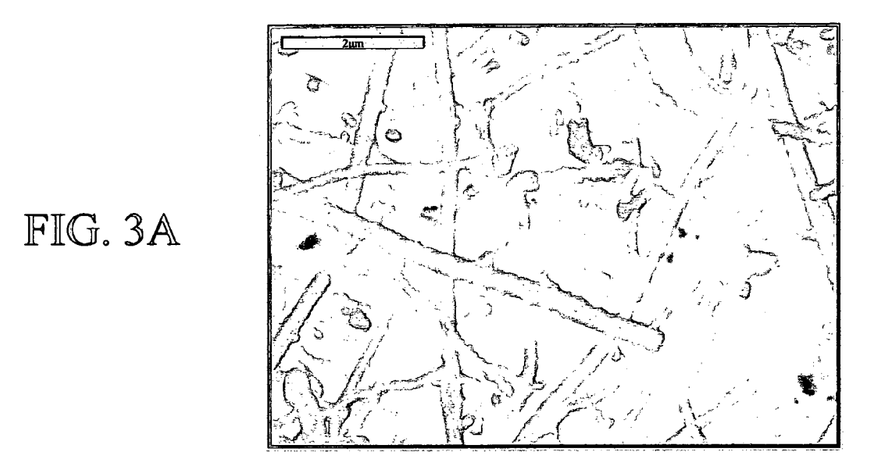
FIGS. 3A-3C show micrographs of calcium carbonate fibers of the present invention extending from a crystalline substrate (calcite rhombs).
Figure 3B:
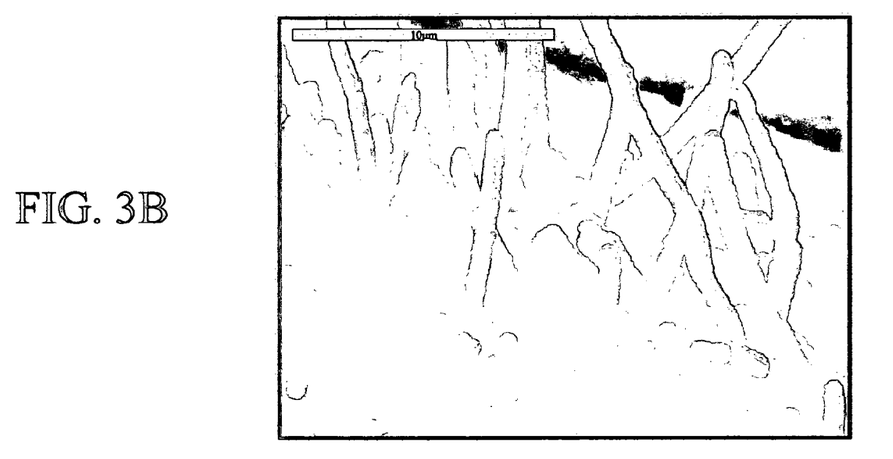
Figure 3C:
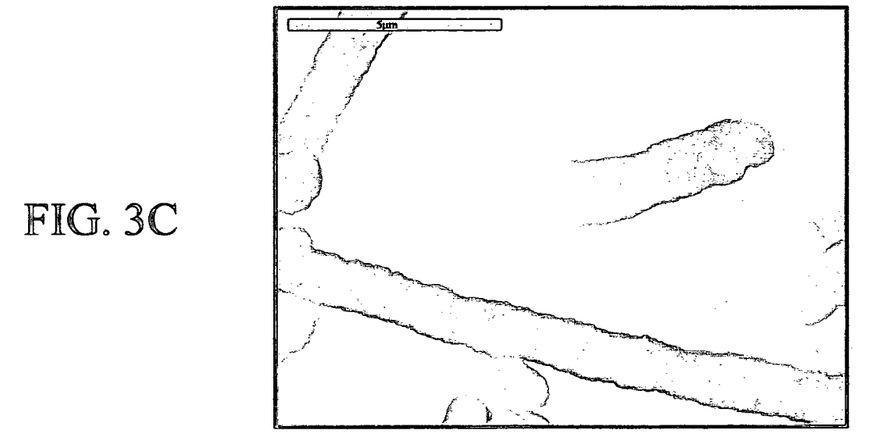
Figure 4A:
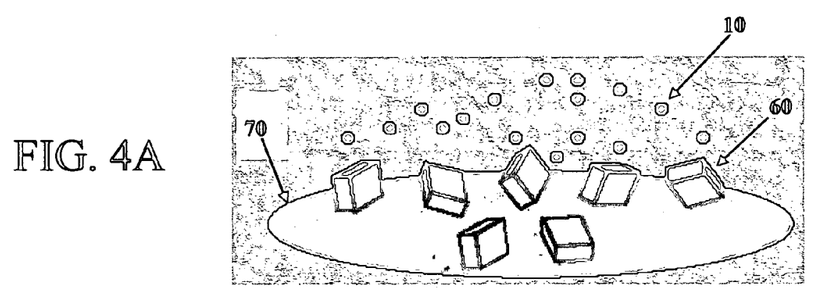
FIGS. 4A-4K show a schematic representation of mineral fiber formation with integrated micrographs of calcite rhombs 60 nucleated on a surface 70 (forming a crystalline inorganic substrate), PILP droplets 10 adsorbing to a rhomb substrate 60 (FIGS. 4A-4E), and fibers 40 forming therefrom (FIGS. 4F-4K).
Figure 4B:
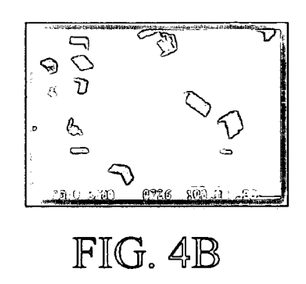
Figure 4C:
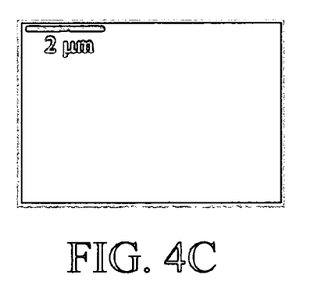
Figure 4D:
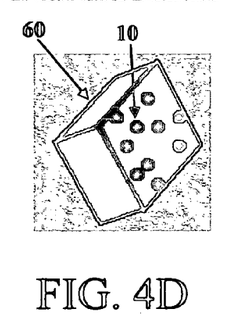
Figure 4E:
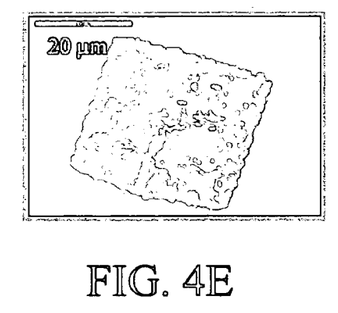
Figure 4F:
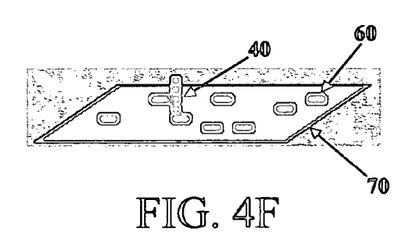
Figure 4G:
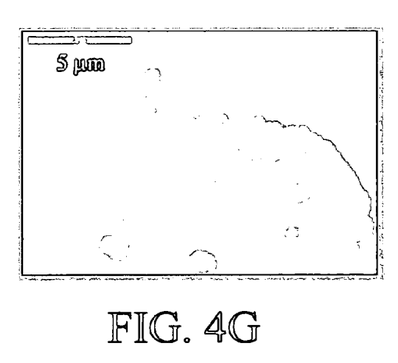
Figure 4H:
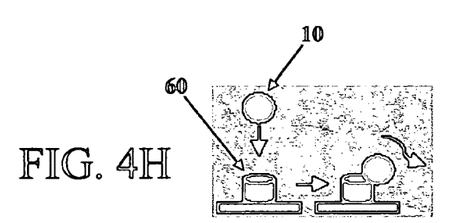
Figure 4I:
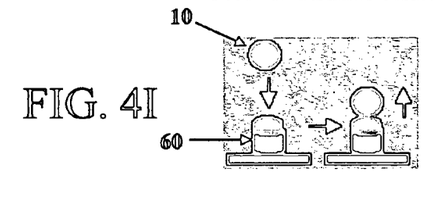
Figure 4J:
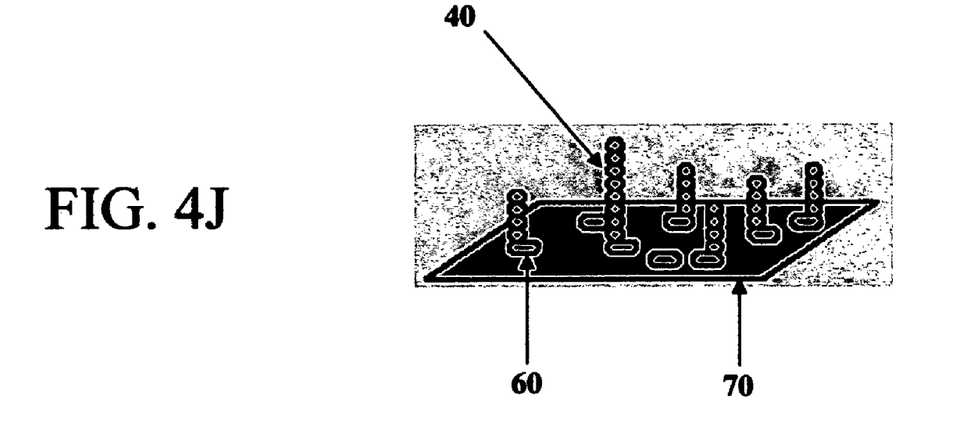
Figure 4K:
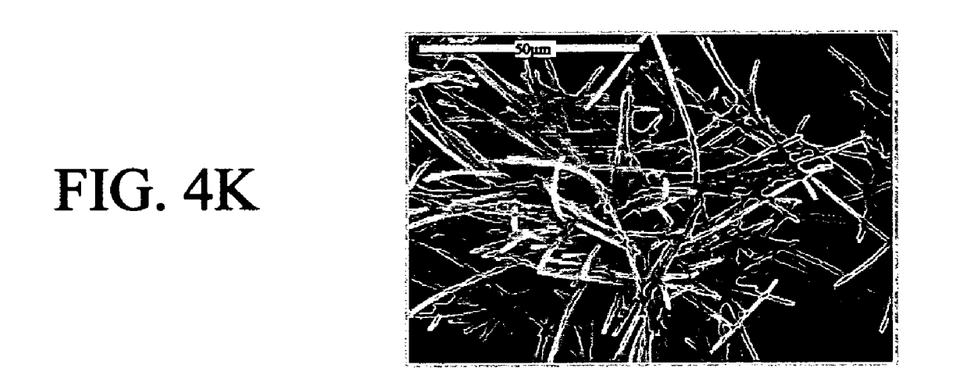
Figure 5A:
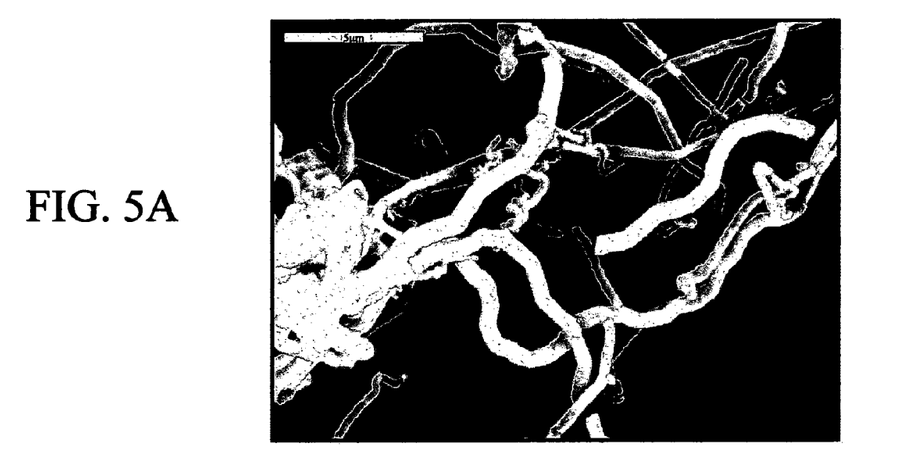
FIGS. 5A-5C show micrographs of serpentine fibers produced by the mechanism of the present invention (which resemble serpentine fibers of semiconductor materials produced by the VLS and SLS mechanisms) (FIG. 5A) and bobble tips on the fibers of the present invention (FIGS. 5B and 5C) resembling the "flux" droplets observed in VLS/SLS mechanisms.
Figure 5B:
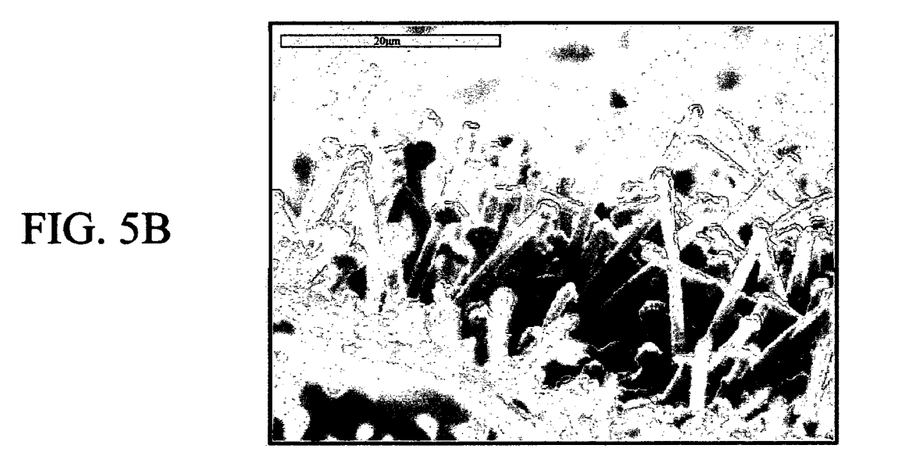
Figure 5C:
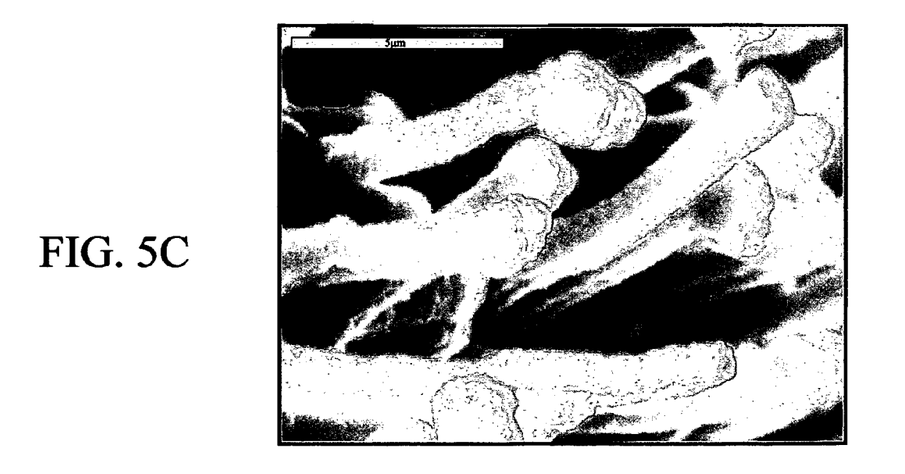

Using the growth mechanisms as a model, it was hypothesized that the calcite fibers disclosed herein are grown in a similar manner, but without a molten metal flux. Instead, they can be formed in an aqueous solution at low temperature. The amorphous liquid-precursor (PILP) droplets begin to deposit on the mineral face and either solidify or remain partially liquid-like. If the primary droplets solidify, subsequent droplets wick to the side of these droplets and form a film. On the other hand, primary droplets that remain liquid-like can further coalesce with subsequent droplets, at which time the primary droplets in contact with the crystalline surface begin to solidify and crystallize. The top droplet remains a liquid while the bottom becomes solid, thus forcing the fiber outward from the crystalline substrate. As long as the leading "flux" droplet (which appears as a bobble on the end of the fiber) remains as a liquid, the fiber will continue to grow. The mechanism is demonstrated in the schematic of FIGS. 1A-1D and FIGS. 4A-4K. The present inventors have named this process the solution-precursor-solid (SPS) mechanism. It is similar to the VLS and SLS mechanisms in the sense that a "flux" droplet restricts crystal growth to one dimension to form a fiber; yet it differs in that the "flux" droplet is not a molten metal, but instead is comprised of a PILP phase, which enables fibers to be formed in aqueous solutions and at much lower temperatures (such as room temperature and below). FIGS. 3A-3C and 5A-5C show micrographs of calcium carbonate fibers of the present invention.

EXAMPLE 2

Hydroxyapatite (HA) Fibers

Enamel, the hardest known vertebrate tissue, is comprised of "rods" of hydroxyapatite tightly packed together in an organized array. Enamel and dentin share a unique starting point, the dentino-enamel junction (DEJ), with the enamel growing away from the DEJ to serve as the mastication surface, and the dentin growing in towards the pulp. While researchers agree that dentine is the first to appear, there is still debate as to whether the enamel epitaxially nucleates from the dentine surface (G. W. Bernard, Ultrastructural observations of initial calcification in dentin and enamel. *Journal of Ultrastructure Research* 41, 1 (1972).; E. J. Reith, Early stage of amelogenesis as observed in molar teeth of Yorun rats. *Journal of Ultrastructure Research* 17, 503 (1967).; P. Bodier-Houlle, P. Steuer, J. M. Meyer, L. Bigeard, F. J. G. Cuisinier, High-resolution electron-microscopic study of the relationship between human enamel and dentin crystals at the dentinoenamel junction. *Cell and Tissue Research* 301, 389 (September, 2000); T. Diekwisch, B. J. Berman, S. Gentner, H. C. Slavkin, Initial enamel crystals are not associated with mineralized dentin. *Journal of Dental Research* 73, 112 (1994)). Additionally, there are reports that there are poorly crystalline or amorphous regions between dentin and enamel (P. Bodier-Houlle, P. Steuer, J. M. Meyer, L. Bigeard, F. J. G. Cuisinier, High-resolution electron-microscopic study of the relationship between human enamel and dentin crystals at the dentinoenamel junction. *Cell and Tissue Research* 301, 389 (September, 2000)). These observations led the present inventors to believe that hydroxyapatite fibers resembling enamel can be recreated using a liquid-amorphous mineral precursor deposited upon hydroxyapatite substrates.

Hydroxyapatite crystals can be nucleated on glass slides via direct addition of calcium chloride and ammonium phosphate at 80° C. The $CaPO_4$ PILP process involves using a 1 mM $CaCl_2.2H_2O$ solution in combination with 200 µg/mL Poly(αβ-DL-Aspartic acid) [Polyasp] and 200 µg/mL Poly (vinyl phosphonic acid) [PVPA]. The glass slides with the hydroxyapatite crystals are placed in the mineralizing solution. This solution is then placed, uncovered, in a desiccator with three equal sized petri dishes, uncovered, and filled with crushed diammonium hydrogen phosphate.

Uncovered is stressed in this explanation because in the $CaCO_3$ PILP process, all of the dishes are preferably covered in such a way to allow diffusion (e.g., covered with parafilm into which three holes are punched). The ammonium phosphate decomposes much slower than the ammonium carbonate; therefore the reaction kinetics have to be increased. The ammonium phosphate slowly decomposes and feeds the counterion into the mineralizing solution. The samples are left to mineralize between 1-4 weeks at which time they are removed from solution and rinsed in both water and ethanol to remove any soluble salts.

What is claimed is:

1. A method for producing a mineral fiber, said method comprising:
  (a) contacting droplets of an inorganic liquid-phase mineral precursor comprising an acidic polymer with a crystalline inorganic substrate in an aqueous solution; and (b) permitting the droplets to deposit onto the surface of the crystalline inorganic substrate, where the droplets coalesce and solidify to form said mineral fiber extending away from the crystalline inorganic substrate.

2. The method according to claim 1, wherein the formed mineral fiber exhibits a single crystalline birefringence.

3. The method according to claim 1, wherein the formed mineral fiber exhibits a single crystalline electron diffraction pattern.

4. The method according to claim 1, wherein the crystalline inorganic substrate comprises a mineral.

5. The method according to claim 1, wherein the crystalline inorganic substrate comprises calcite rhombs.

6. The method according to claim 1, wherein the crystalline inorganic substrate comprises a mineral thin film.

7. The method according to claim 6, wherein the thin film is a patterned thin film.

8. The method according to claim 6, wherein the thin film comprises at least one member selected from the group consisting of $CaCO_3$, $CaPO_4$, $BaCO_3$, and $SrCO_3$.

9. The method according to claim 5, wherein the calcite rhombs are nucleated on a solid surface.

10. The method according to claim 1, wherein the crystalline inorganic substrate comprises crystals of hydroxyapatite.

11. The method according to claim 1, wherein said method further comprises forming the inorganic liquid-phase mineral precursor by contacting an acidic polymer with a mineralizing solution under conditions permitting formation of the inorganic liquid-phase mineral precursor.

12. The method according to claim 11, wherein the acidic polymer comprises at least one member selected from the group consisting of polyacrylic acid, polymethacrylic acid, sulfonated polymer, phosphorylated proteins or peptides, phosphorylated synthetic polymers, sulfated polysaccharides, sulfated glycoproteins, polyaspartic acid, polyglutamic acid, polyaspartate, polyvinyl phosphate, and polyvinyl phospbonate, or combinations of any of the foregoing.

13. The method according to claim 1, wherein the inorganic liquid-phase mineral precursor comprises at least one member selected from the group consisting of calcium phosphate, calcium carbonate, hydroxyapatite, strontium carbonate, barium carbonate, and calcium sulfate, strontium sulfate, calcium oxalate, magnesium-bearing calcium carbonate, and magnesium-bearing calcium phosphate.

14. The method according to claim 1, wherein the inorganic liquid-phase mineral precursor comprises at least one member selected from the group consisting of hydroxyapatite, octacalcium phosphate, tricalcium phosphate, carbonated hydroxyapatite, fluorinated hydroxyapatite, brushite, magnesium containing hydroxyapatite, dicalcium phosphate dihydrate, and amorphous calcium phosphate.

15. The method according to claim 1, wherein said method further comprises associating a biologically active agent with the fiber.

16. The method according to claim 15, wherein the biologically active agent comprises at least one member selected from the group consisting of medicaments; vitamins; mineral supplements; substances used for the treatment, prevention, diagnosis, cure or mitigation of disease or illness; substances affecting the structure or function of the body; drugs; antimicrobial agents; antifungal agents; antibacterial agents; antiviral agents; antiparasitic agents; growth factors; angiogenic factors; anaesthetics; mucopolysaccharides; metals; cells; acid mucopolysaccharides; proteins; enzymes; peptides; and wound healing agents.

17. The method according to claim 1, wherein said method further comprises forming the inorganic liquid-phase mineral precursor by combining calcium salt and an acidic polymer to form an aqueous solution, and reacting the aqueous solution with ammonium carbonate vapor or ammonium phosphate vapor.

18. The method according to claim 17, wherein the aqueous solution is reacted with the ammonium carbonate vapor, and wherein the ammonium carbonate vapor is provided through the decomposition of at least one ammonium carbonate material selected from the group consisting of ammonium carbonate monohydrate, ammonium carbonate dihydrate, and ammonium carbamate.

19. The method according to claim 17, wherein the aqueous solution is reacted with the ammonium phosphate vapor, and wherein the ammonium phosphate vapor is provided through the decomposition of at least one ammonium phosphate material selected from the group consisting of ammonium phosphate monobasic, ammonium phosphate dibasic.

20. The method according to claim 1, wherein said method further comprises forming the inorganic liquid-phase mineral precursor by combining calcium chloride and a combination of acidic polymers to form an aqueous solution, and reacting the aqueous solution with ammonium phosphate vapor.

21. The method according to claim 1, wherein said method further comprises forming the inorganic liquid-phase mineral precursor by combining calcium chloride and a combination of acidic polymers to form an aqueous solution, and reacting said aqueous solution with a phosphate containing solution.

22. The method according to claim 1, wherein said method further comprises forming the inorganic liquid-phase mineral precursor by combining calcium salt and a combination of acidic polymers to form an aqueous solution, and reacting said aqueous solution with phosphate generated by enzymatic degradation of phosphate containing compounds.

23. The method according to claim 1, wherein said method further comprises forming the inorganic liquid-phase mineral precursor by combining calcium salt and ammonium phosphate, and a combination of acidic polymers to form an aqueous solution, in which precipitation is caused by at least one of the following conditions: a change of temperature, a change of pH, evaporation, or removal of crystallization inhibitor.

24. The method according to claim 1, wherein said contacting of the inorganic liquid-phase mineral precursor with the crystalline inorganic substrate is carried out at a temperature of 4° C. or higher.

25. The method according to claim 1, wherein the droplets of inorganic liquid-phase mineral precursor comprise primary droplets that contact the crystalline inorganic substrate and secondary droplets that contact the primary droplets, and wherein the secondary droplets extend the length of the mineral fiber.

26. The method according to claim 1, wherein the inorganic liquid-phase mineral precursor comprises hydroxyapatite, and wherein the inorganic crystalline substrate comprises a hydroxyapatite film.

27. The method according to claim 1, wherein the formed fiber has an aspect ratio in the range of about 5 (5:1) to 60 (60:1).

28. The method according to claim 1, wherein the formed fiber comprises a mineral phase that is homogenously distributed throughout the width of the fiber.

29. The method according to claim 1, wherein the inorganic liquid-phase mineral precursor crystallizes in an epitaxial orientation.

30. The method according to claim 1, wherein the inorganic liquid-phase mineral precursor does not comprise a metal flux.

31. A mineral fiber produced by the method of claim 1.

32. A pharmaceutical composition comprising a mineral fiber produced by the method of claim 1, and a pharmaceutically acceptable carrier.

33. A method for treating a tissue defect within a patient, said method comprising applying an effective amount of a mineral fiber to the site of the tissue defect, wherein the mineral fiber is produced according to the method of claim 1.

* * * * *

UNITED STATES PATENT AND TRADEMARK OFFICE
CERTIFICATE OF CORRECTION

PATENT NO. : 7,455,854 B2
APPLICATION NO. : 10/819040
DATED : November 25, 2008
INVENTOR(S) : Gower et al.

It is certified that error appears in the above-identified patent and that said Letters Patent is hereby corrected as shown below:

Column 12,
Line 60 "$Na_2 O_3Si.9H_2O$" should read --$Na_2 O_3Si \cdot 9H_2O$--.

Column 13,
Line 32 "$MgCl_2.6H_2O$ or $SrCl_2.6H_2O$" should read --$MgCl_2 \cdot 6H_2O$ or $SrCl_2 \cdot 6H_2O$--.

Column 16,
Line 44 "$CaCl_2.2H_2O$" should read --$CaCl_2 \cdot 2H_2O$--.

Column 17,
Line 37 "phospbonate" should read --phosphonate--.

Signed and Sealed this
Fourteenth Day of June, 2011

David J. Kappos
*Director of the United States Patent and Trademark Office*